United States Patent
Liu et al.

(10) Patent No.: US 9,675,563 B2
(45) Date of Patent: Jun. 13, 2017

(54) METHOD FOR ADJUNCTIVE TREATMENT OF CANCER METASTASIS BY USING LYCOGEN

(71) Applicant: ASIA-PACIFIC BIOTECH DEVELOPING, INC., Kaohsiung (TW)

(72) Inventors: Wen-Sheng Liu, Kaohsiung (TW); Fu-Hsin Chang, Kaohsiung (TW); Ya-Fen Hsiao, Kaohsiung (TW)

(73) Assignee: ASIA-PACIFIC BIOTECH DEVELOPING, INC., Kaohsiung (TW)

( * ) Notice: Subject to any disclaimer, the term of this patent is extended or adjusted under 35 U.S.C. 154(b) by 0 days.

(21) Appl. No.: 15/221,627

(22) Filed: Jul. 28, 2016

(65) Prior Publication Data

US 2017/0027883 A1    Feb. 2, 2017

(30) Foreign Application Priority Data

Jul. 30, 2015   (TW) .............................. 104124792 A (51) Int. Cl.
*A61K 31/121*   (2006.01)
*A61K 35/74*   (2015.01)

(52) U.S. Cl.
CPC ............ *A61K 31/121* (2013.01); *A61K 35/74* (2013.01)

(58) Field of Classification Search
CPC ............................. A61K 31/121; A61K 35/74
USPC ........................................................ 514/675
See application file for complete search history.

(56) References Cited

U.S. PATENT DOCUMENTS 8,563,267 B2 * 10/2013 Liu ......................... A61K 8/99
435/252.3

\* cited by examiner

*Primary Examiner* — Yevegeny Valenrod
(74) *Attorney, Agent, or Firm* — Hannah M. Tien (57) ABSTRACT

The present invention relates to a method for adjunctive treatment of cancer by using a Lycogen composition to inhibit metastasis, comprising administering a Lycogen composition to the subject, wherein the Lycogen composition comprises an effective amount of a Lycogen extract, wherein the Lycogen extract comprises active ingredients selected from ζ-carotene, neurosporene, spheroidenone, methoxyneurosporene or a combination thereof.

5 Claims, 10 Drawing Sheets

Fig. 10

METHOD FOR ADJUNCTIVE TREATMENT OF CANCER METASTASIS BY USING LYCOGEN

CROSS-REFERENCES TO RELATED APPLICATIONS

The present application claims priority to Taiwan Patent Application No. 104124792, filed on Jul. 30, 2015, which is incorporated herein by reference in its entirety.

FIELD OF THE INVENTION

The present invention relates to a method for adjunctive treatment of cancer metastasis by using a Lycogen composition.

BACKGROUND OF THE INVENTION

Cancer is the top often leading causes of death in Taiwan. Almost all cancers can become metastatic tumors, and once distant metastasis occurs, cancer cells will disseminate into every part of the body, decreasing cure rate. Cancer cell metastasis is one of the main causes which leads to cancer recurrence and death of cancer patients. Metastasis begins when the adhesion between a cellular matrix and an extracellular matrix changes, the interaction force between cells is destructed, the extracellular matrix is decomposed, and then cancer cells penetrate into the extracellular matrix, invade into blood vessels and lymph vessels of the circulatory system, escape from the immune system, attach to endothelial cells, penetrate through blood vessels and lymph vessels into new tissues and organs, multiply and induce angiogenesis massively. Cancer cells deprive normal tissues and organs of nutrients by newly formed blood vessels causing normal tissues and organs to waste away and ultimately death of cancer patients.

In other words, angiogenesis occurs when tumors produce pro-angiogenic growth factors which induce the formation of new blood vessels, stimulate endothelial cells of blood vessels to undergo angiogenesis, and newly formed blood vessels bring nutrition and oxygen necessary for tumor growth. Over the last few decades, many human and animal researches have confirmed that tumor growth and migration depend on angiogenesis. Therefore, when metastasis and invasion of cancer cells into the circulatory system are inhibited, the death rate of cancer patients due to metastasis is likely to be decreased. The present invention provides a method for adjunctive treatment of cancers by using a Lycogen composition in anticancer drugs to inhibit metastasis.

Previous researches carried out by the inventors suggest that Lycogen can significantly inhibit the secretion of intracellular matrix metalloproteinases-2 (MMP-2). MMP is closely related to angiogenesis of endothelial cells of blood vessels and is the primary component for the formation of new blood vessels in endothelial cells. The main function of MMP includes assisting the migration of endothelial cells and degrading intercellular matrix for the formation of new blood vessels. MMP-2 and MMP-9 are capable of degrading basement membrane matrix type V collagens, which are most closely related to angiogenesis and metastasis. Also, angiogenesis plays an important role in the process of metastasis. Therefore, it is worth to study whether Lycogen inhibits angiogenesis. The present invention further confirms a synergistic effect between the Lycogen and anticancer drugs to inhibit MMP activity and secretion, thereby having adjunctive effects on anticancer drugs.

SUMMARY OF THE INVENTION

The present invention relates to a method for adjunctive treatment of cancer by using a Lycogen composition to inhibit metastasis, comprising administering a Lycogen composition to the subject, wherein the Lycogen composition comprises an effective amount of a Lycogen extract, wherein the Lycogen extract comprises active ingredients selected from ζ-carotene, neurosporene, spheroidenone, methoxyneurosporene or a combination thereof.

DETAILED DESCRIPTION OF THE INVENTION

Lycogen used in the present invention has been disclosed in the U.S. Pat. No. 8,563,267 entitled "LYCOGEN EXTRACT, COMPOSITION THEREOF AND METHOD FOR THE TREATMENT USING THE SAME" which is incorporated herein by reference in its entirety. Lycogen used in the present invention is manufactured according to the examples described in the U.S. Pat. No. 8,563,267. The Lycogen extract comprises active ingredients selected from ζ-carotene, neurosporene, spheroidenone, methoxyneurosporene or a combination thereof. Lycogen is extracted from a mutant photosynthetic bacterium, which is produced by the mutation of a wild or cultivated primary photosynthetic bacterium by ultraviolet irradiation. The mutant photosynthetic bacterium is *Rhodobacter sphaeroides*, which is deposited at the German Collection of Microorganisms and Cell Cultures under the Budapest Treaty, Deposit Number DSM 25056. It is also deposited at the Food Industry Research and Development Institute in Hsinchu, Taiwan, Deposit Number BCRC910406.

In one embodiment, the ζ-carotene is more than 10% by weight of the Lycogen extract. In another embodiment, the neurosporene is more than 10% by weight of the Lycogen extract. In another embodiment, the spheroidenone is more than 30% by weight of the Lycogen extract. In another embodiment, the methoxyneurosporene is more than 30% by weight of the Lycogen extract.

The present invention provides a method for adjunctive inhibition of cancer metastasis by using a Lycogen composition in anticancer drugs, wherein the composition comprises an effective amount of the Lycogen extract. The present invention induces the formation of blood vessels, and evaluates the indices of angiogenesis, including measurements of cell apoptosis, cell migration, tubeformation, MMPs activity, etc. The present invention conducts angiogenesis assays of Lycogen in combination with anticancer drugs and confirms that Lycogen has inhibitory effects on cell tubeformation and can inhibit cell migration and MMP-9 activity. Therefore, Lycogen indeed shows synergistic effects with anticancer drugs, which reduce the required dosage of anticancer drugs and side effects.

In one embodiment, the effective dose of the Lycogen composition used to inhibit cancer cell growth is from 5 to 200 μM. In another embodiment, the effective dose of the Lycogen composition is from 10 to 150 μM. In one preferred embodiment, the effective dose of the Lycogen compositions is 50-100 μM.

In one embodiment, the effective dose of the Lycogen composition used adjunctively with anticancer drug to inhibit cancer metastasis is 2-200 μM. In another embodiment, the effective dose of the Lycogen composition is 5-150 μM. In one preferred embodiment, the effective dose of the Lycogen compositions is 10-100 μM.

The Lycogen composition in the present invention also has the ability of inhibiting cancer metastasis when used alone. It only needs 5 μM of Lycogen to inhibit cancer cell migration and invasion (shown in FIGS. 9 and 10), and therefore inhibit cancer metastasis.

The term "cancer" as used herein means carcinoma, sarcomas, adenocarcinoma, lymphoma, leukemia, solid cancers, lymphatic cancer, etc. Different types of cancer examples include, but are not limited to, lung cancer (such as non-small cell lung cancer or NSCLC), ovarian cancer, prostate cancer, colon and rectal cancer, liver cancer (i.e. hepatocarcinoma), kidney cancer (i.e. renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, carcinoid tumors of the gastrointestinal tract, esophageal cancer, gallbladder cancer, appendiceal cancer, cancer of small intestine, gastric cancer, cancer of central nervous system, skin cancer, chorionic carcinoma, head and neck cancers, leukemia, osteogenic sarcoma, fibrosarcoma, neuroblastoma, neuroglial tumor, melanoma, B cell lymphoma, non-Hodgkin's lymphoma, Burkitt's lymphoma, small cell lymphoma, big cell lymphoma, monocytic leukemia, myelogenous leukemia, acute lymphocytic leukemia, acute myelogenous leukemia (AML), chronic myelogenous leukemia (CML), and multiple myeloma. In some specific embodiments, the compositions and the method provided by the present invention are effective in treating cancers.

EXAMPLES

The present invention may be implemented in many different forms and should not be construed as limited to the examples set forth herein; one skilled in the art may modify and vary the examples without departing from the spirit and scope of the present invention, therefore, the examples should not be construed as the limitation of the claims.

Lycogen Used for Adjunctive Inhibition of Cancer Metastasis

Cell Proliferation Analysis

In one example, Lycogen was dissolved in tetrahydrofuran (THF) to form various concentrations of Lycogen reagents (0, 10, 50, 100 μM), which are used for cultivating HUVEC cells for 24-72 hours, at least three times for each group, and then MTT assay was conducted for cell proliferation analysis. The assay results were presented in percentage.

Figure 9:
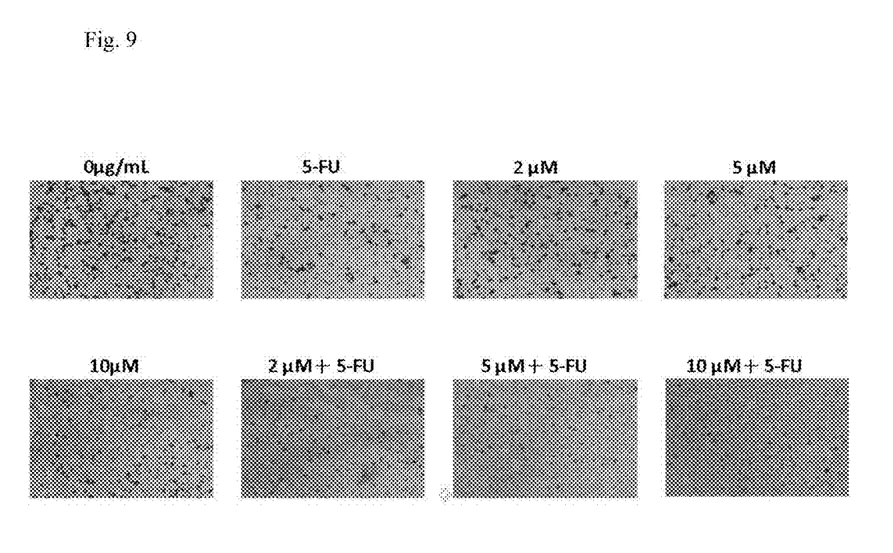
FIG. 9 shows the fluorescent microscope results of Lycogen used with 5-FU on cancer cell invasion.

FIG. 9 showed that after HUVEC cells were cultivated with the Lycogen reagent for 24-72 hours, the number of HUVEC cell was significantly decreased as doses and time increased. When HUVEC cells were cultivated with 10 μM of the Lycogen reagent for 24-48 hours, no significant toxicity was observed. After being cultivated with 50 μM of the Lycogen reagent for 48 hours the proliferation of HUVEC cells was significantly inhibited. When 100 μM of the Lycogen reagent was used to cultivate HUVEC cells, the inhibition of proliferation of HUVEC cells occurred at 24 hours after being cultivated. The results could be used as a reference of the dose the Lycogen reagent and the cultivation time.

Angiogenesis Assay

The in vitro angiogenesis assay was a model test used for studying anti-angiogenic nutrient or drugs, and the assay was highly convenient and fast. Accordingly, the in vitro angiogenesis assay was used to study whether Lycogen exhibited synergistic effects on the inhibition of HUVEC cell tubeformation. $H_2O_2$ was used to induce tubeformation in matrigel to evaluate the effect of Lycogen on the index of angiogenesis. HUVEC cells were dissolved in 10% serum-containing culture media, and then HUVEC cells were seeded into matrigel pre-coated 24-well plates in a density of 1*10 cells per well. Except for the control group HUVEC cells in all other groups were treated with solvent vehicle, 5-FU, 5-FU plus 10 μM Lycogen, 5-FU plus 30 μM Lycogen, and 5-FU plus 50 μM of Lycogen, respectively. Each assay under the same experimental condition was performed in duplicate and this experiment was repeated twice. Phase contrast photomicrographs were taken by a phase contrast microscope with 100× magnification at 6 hours after the treatment.

Figure 10:
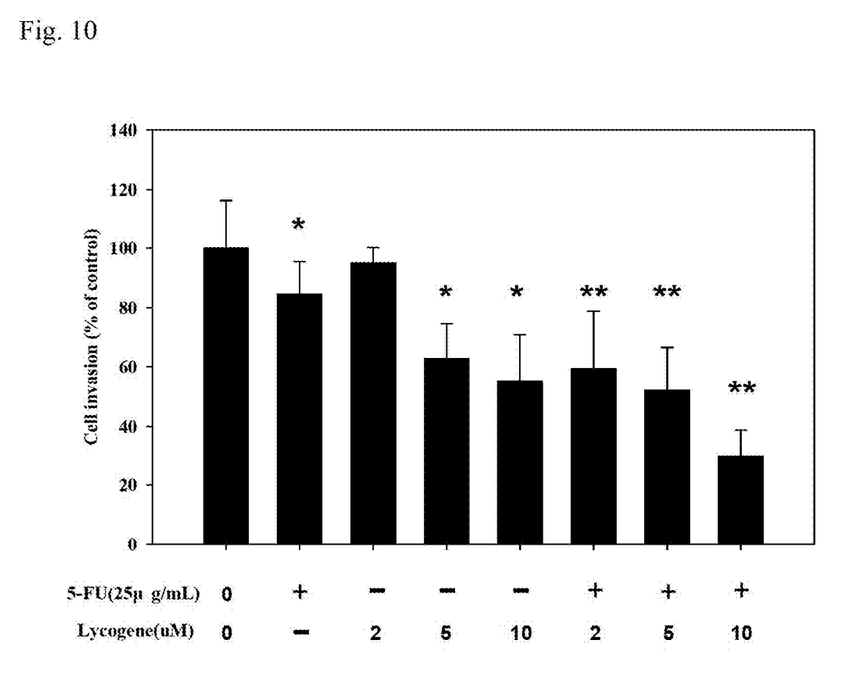
FIG. 10 shows the analysis results of inhibitory effects of Lycogen used with 5-FU on cancer cell invasion.

FIG. 10 showed that $H_2O_2$ in fact induced the cell tubeformation, and the effect of the solvent group on the tubeformation was similar to that of the control group, which meant the solvent did not affect the assay. Besides, 5-FU did inhibit the cell tubeformation. When 5-FU was combined with various concentrations of Lycogen (10-30 μM), 5-FU exhibited higher inhibitory effects on tubeformation as the concentration of Lycogen was increased.

Cell Migration Analysis

In another example, the effect of Lycogen on cell migration was analyzed under the same conditions of the aforementioned angiogenesis analysis. FIG. 11 showed that 5-FU did inhibit the ability of cell migration. When various concentration of Lycogen were added into 5-FU (THF was used as the solvent to prepare 10-50 μM of Lycogen), as the dose of Lycogen increased the number of migrated cells decreased, which meant that Lycogen had adjunctive effect on the capability of 5-FU to inhibit the cell migration.

In another example, the effect of Lycogen on cell migration in human umbilical vein endothelial cell line (EA.hy926 cell line) was analyzed. The cell line was treated with different concentrations of Lycogen (0, 2, 5, and 10 μM) or 25 μg/mL 5-FU, and the EA.hy926 cell migration was analyzed 24 hours after treatments to calculate the migration areas.

Figure 1:
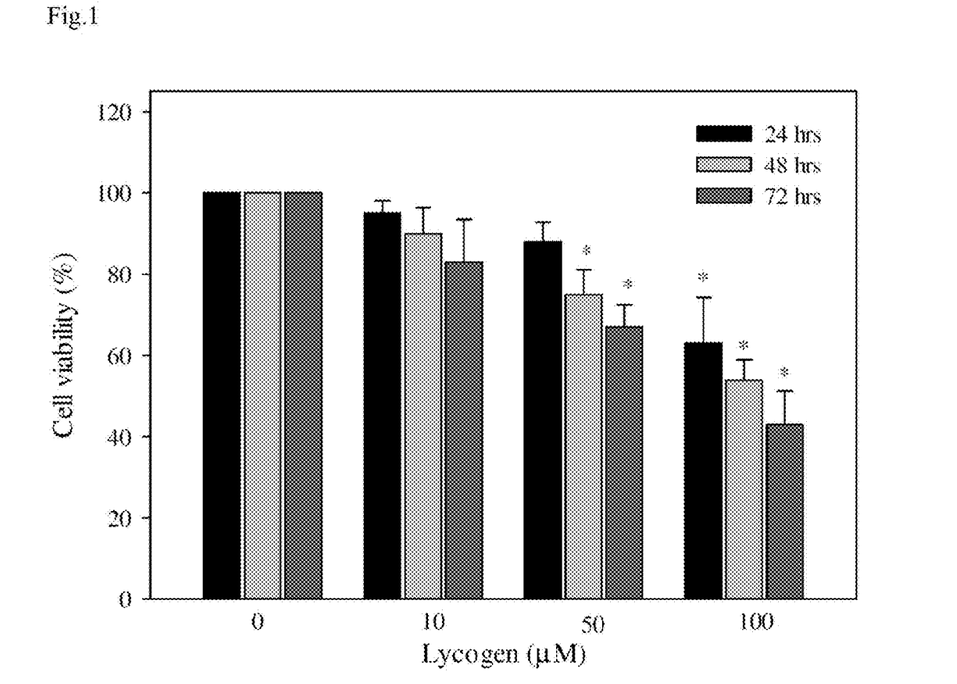
FIG. 1 shows the result of inhibition of cell proliferation by Lycogen.
Figure 2:
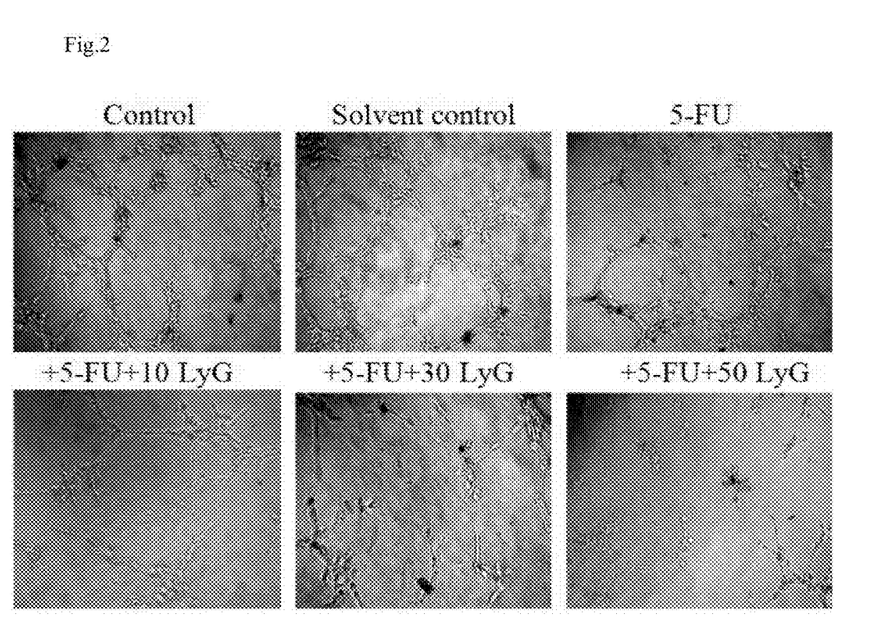
FIG. 2 shows the inhibitory effects of Lycogen and 5-FU on angiogenesis.
Figure 3:
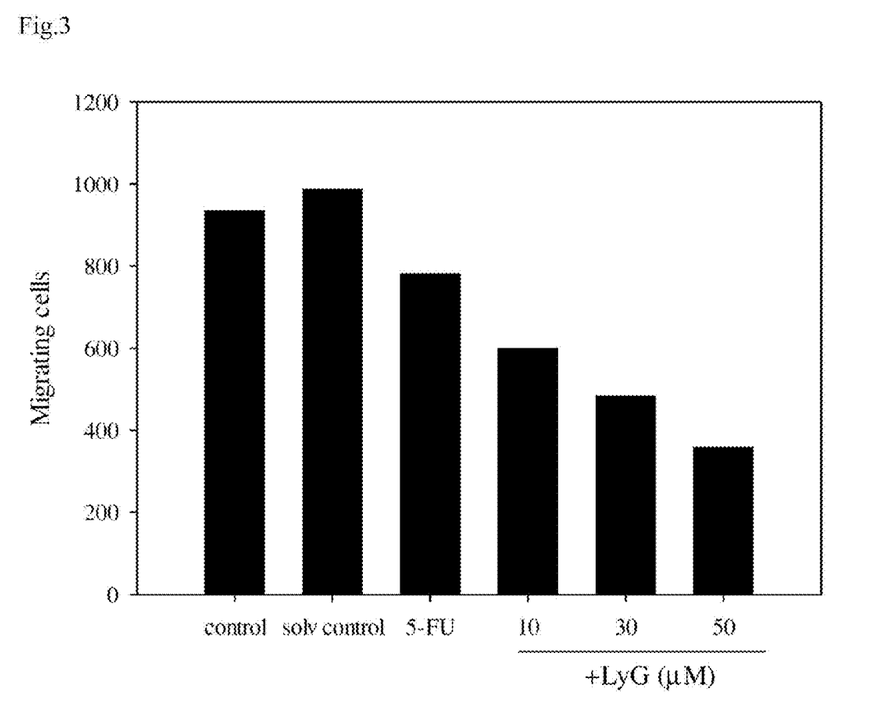
FIG. 3 shows the inhibitory effects of Lycogen and 5-FU on cell migration.
Figure 4:
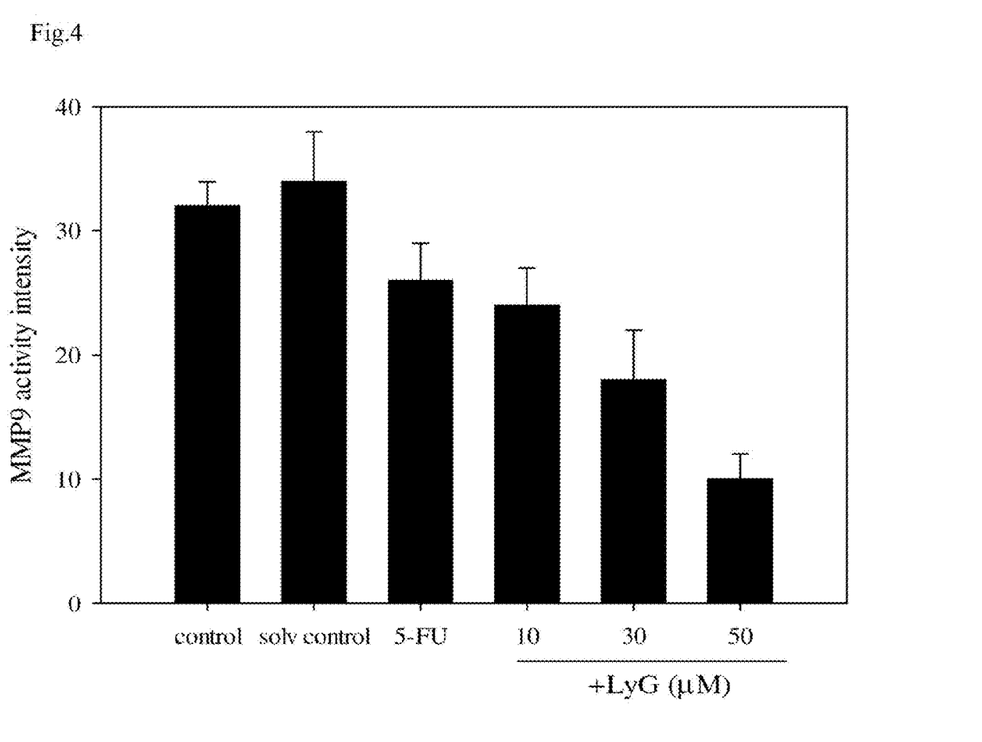
FIG. 4 shows the inhibitory effects of Lycogen and 5-FU on MMP-9 activity.
Figure 5:
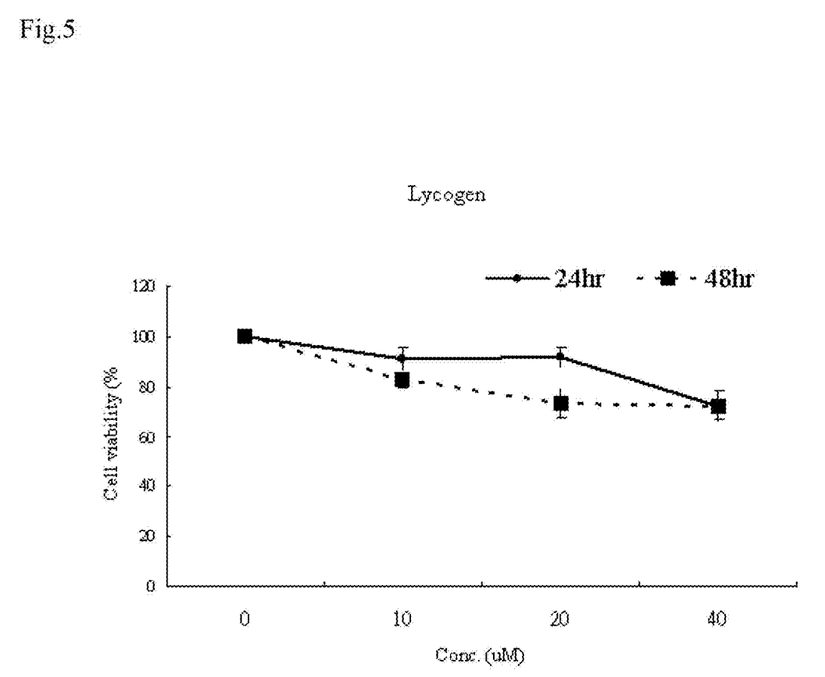
FIG. 5 shows Lycogen concentrations and cell survival rate.
Figure 6:
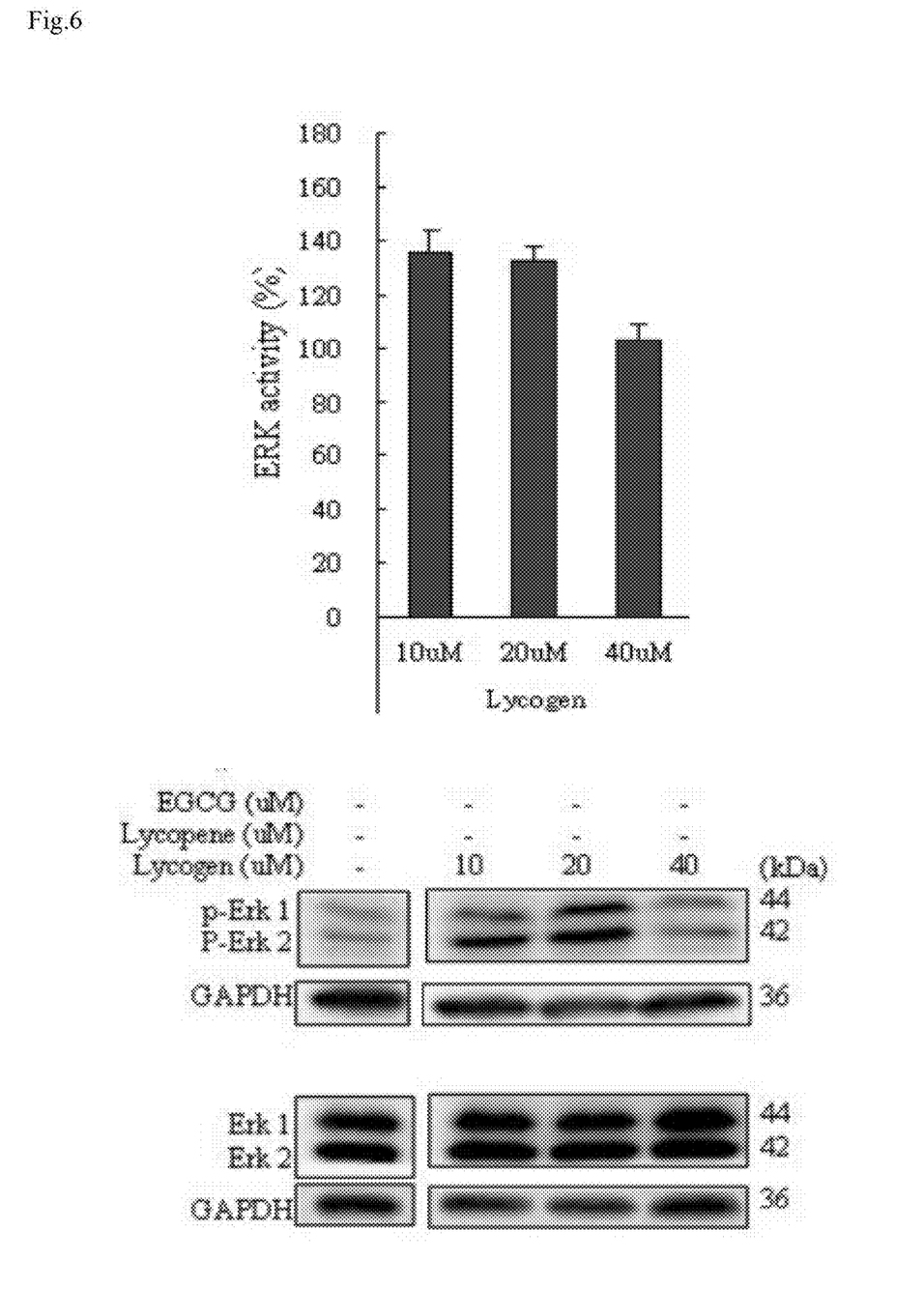
FIG. 6 shows the immunostaining analysis of ERK protein activity.
Figure 7:
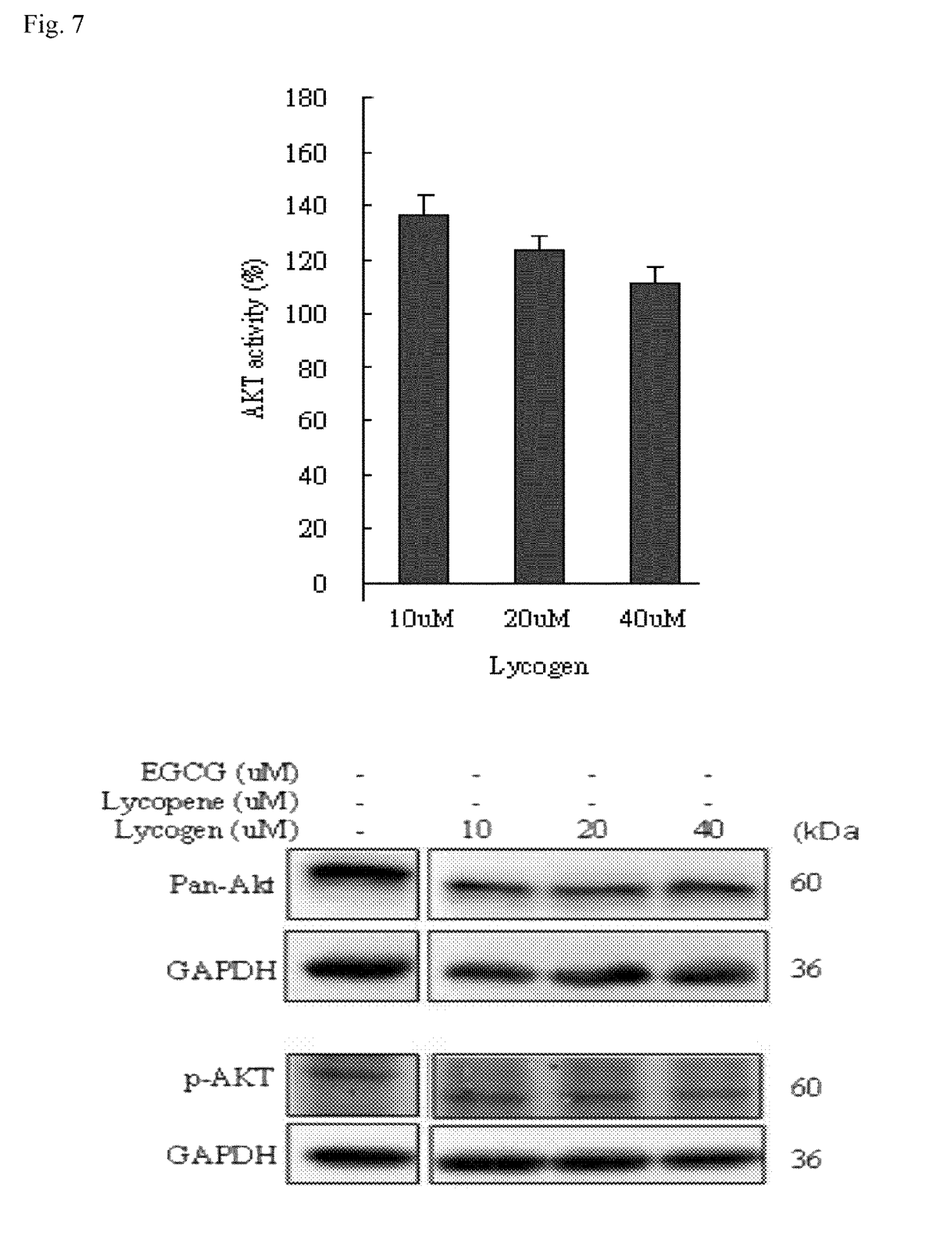
FIG. 7 shows the immunostaining analysis of AKT protein activity.
Figure 8:
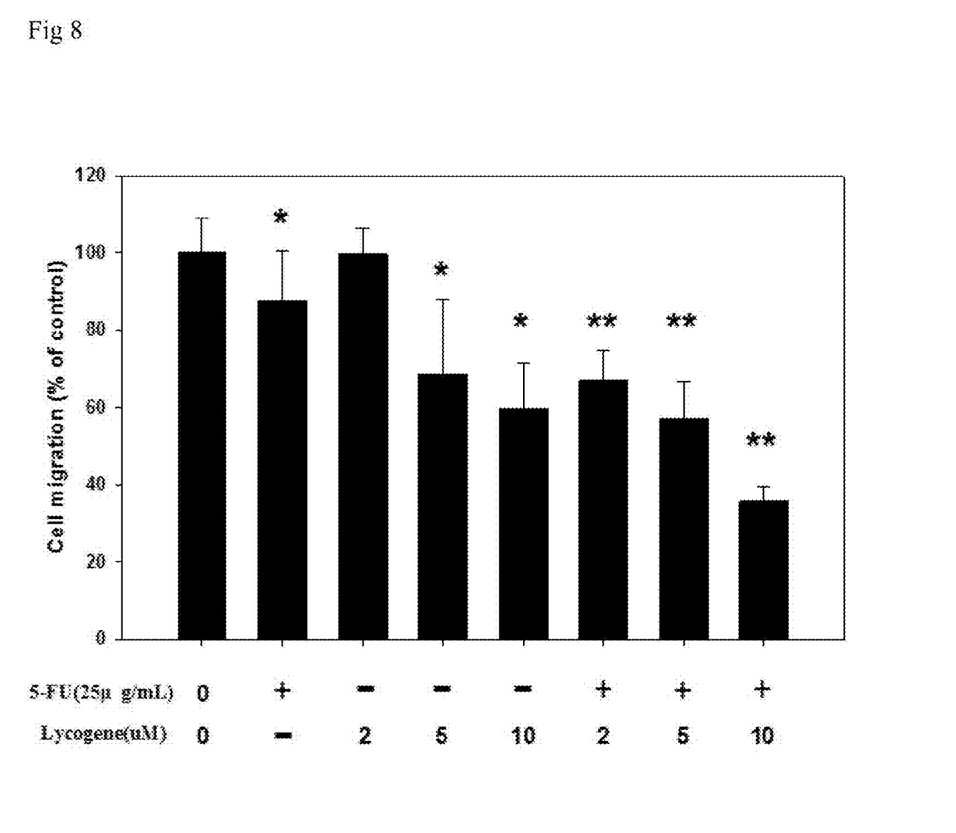
FIG. 8 shows the analysis results of inhibitory effects of Lycogen used with 5-FU on cancer cell migration.

FIG. 8 showed that 5-FU, and 5 and 10 μM Lycogen had the ability of inhibiting cancer cell migration. Furthermore, just 2 μM of Lycogen administered together with 5-FU could significantly increase the inhibitory effect of cancer cell migration.

MMP-9 Activity Analysis

Matrix metalloproteinase (MMP) was closely related with angiogenesis of endothelial cells of blood vessels and was the primary component of the newly formed blood vessels in endothelial cells. The main function of MMP was to assist endothelial cells migration and to degrade intercellular matrix to facilitate the formation of new blood vessels. Among all MMPs, MMP-2 and MMP-9 were most closely related with angiogenesis. MMPs in cancer cells were activated by active oxygen to increase their synthesis and secretion, which were used to facilitate local invasion and distant metastasis so that cancer cells could penetrate through basement membrane and from blood vessels into tissues for metastasis. In another example, the activity of MMP-9 was analyzed. FIG. 12 showed that the combined use of Lycogen and 5-FU could inhibit the activity of MMP-9 and was dose dependent, i.e. the dose of Lycogen was higher, the activity of MMP-9 was lower.

Cancer Cell Invasion Assay

In one embodiment, the EA.hy926 cell line was used to analyze the ability of Lycogen on inhibiting cancer cell invasion. EA.hy926 cell line was treated with various concentration of Lycogen (0, 2, 5, and 10 μM) or 25 μg/mL 5-FU. Twenty-four hours after treatment, the Matrigel was used to analyze the cell invasion, and fluorescent microscope was used to observe the cancer cell invasion.

Cells were cultured on the plate, which was covered by a semipermeable membrane, to mimic the condition of cell invasion in vivo. The basal membrane was interrupted in invasive tumor cell to invade adjacent tissue. The cell culture plate was scratched by a sterile tip or cotton thread to create an acellular space. The cell lines were treated with different treatments, and then the cell number inside the membrane was counted.

FIGS. 9 and 10 showed that the invaded cell number significantly decreased in 5-FU treated group (compared to 0 μg/ml group). The invaded cell numbers in 2, 5, and 10 μM of Lycogen treated groups also significantly decreased. Moreover, just 2 μM of Lycogen administered together with 5-FU could significantly increase the inhibitory effect of cancer cell invasion, indicating that the Lycogen had significant synergistic effect with anticancer drug to inhibit cancer cell invasion.

Analysis of Lycogen Used for Adjunctive Inhibition of Cancer Metastasis

Inhibition of Cancer Cell Proliferation Assay

In another preferred example, prostate cancer cell lines DU145 and LNCap were used to observe the inhibitory effect of Lycogen on cancer cell proliferation. One-way ANOVA and Independent Sample T-Test statistical analysis were used for analysis.

After the prostate cancer cell lines DU145 were treated by an antioxidant Epigallocatechin gallate (EGCG) for 24 and 48 hours, analyses were conducted. As shown in table 1, Lycogen significantly inhibit cell proliferation of the prostate cancer cells (p<0.05). The results showed that Lycogen had faster inhibitory effects on the prostate cancer cell lines DU145. In the cell lines LNCap assay, when treated for less than 48 hours, Lycogen also showed significant inhibitory effect on the cancer cells (p<0.05). The results showed that Lycogen was capable of inhibiting the survival of prostate cancer cells.

TABLE 1

Significance analysis of prostate cancer cell survival rate using one-way ANOVA

|  | 24 hrs | | | 48 hrs | | |
| --- | --- | --- | --- | --- | --- | --- |
|  | df | F | p-value | df | F | p-value |
|  | DU145 | | | | | |
| Lycogen | 4 | 7.135 | 0.002 | 4 | 5.985 | 0.004 |
|  | LNCaP | | | | | |
| Lycogen | 4 | 10818 | 0.202 | 4 | 6.845 | 0.006 |

Various concentrations of Lycogen were tested to analyze the effect of Lycogen on the survival rate of the DU145 cells. FIG. 13 showed that in the prostate cancer cell lines DU145, when the concentration of Lycogen was higher, the survival rate of prostate cancer cells was lower.

By using Independent Sample T-Test, the significance analysis showed that, as shown in Table 2, at 24 hours of the treatment, Lycogen effectively inhibited DU145 cell growth at 40 μM, and at 48 hours after the treatment, Lycogen effectively inhibited DU145 cell growth at from 5 to 40 μM.

|  | DU145 | | | |
| --- | --- | --- | --- | --- |
|  | 24 hrs | | 48 hrs | |
| Lycogen | p-value | 95% Confidence Interval | p-value | 95% Confidence Interval |
| 5 uM | 0.164 | −0.021~0.102 | 0.015 | 0.055~0.352 |
| 10 uM | 0.128 | −0.017~0.107 | 0.033 | 0.015~0.265 |
| 20 uM | 0.211 | −0.033~0.117 | 0.006 | 0.089~0.346 |
| 40 uM | <0.001 | 0.093~0.184 | 0.007 | 0.104~0.393 |

Lycogen Used for the Test of Inhibition of ERK and AKT Activity in Prostate Cancer Cells In another example, the relative protein activities were analyzed, including the protein activities of ERK and AKT. AKT was involved in the cell survival pathway through the process of apoptosis inhibition. AKT was capable of blocking apoptosis and stimulate cell survival, and many studies had thus confirmed that AKT had essential functions in a plurality of tumors. ERK could interact with many transcription factors, phosphate kinases, phosphatases, apoptosis proteins so that when the ERK signal transduction pathway was activated, cell proliferation and survival were induced, causing tumor growth.

FIG. 14 and FIG. 15 showed that Lycogen was able to inhibit the protein activities of ERK and AKT, wherein the protein activities were inhibited by the inhibition of ERK and AKT phosphorylation reactions.

What is claimed is:

1. A method for adjunctively treating cancer metastasis in a subject, comprising administering a Lycogen composition to the subject, wherein the Lycogen composition comprises an effective amount of a Lycogen extract.

2. The method of claim 1, wherein the Lycogen extract comprises active ingredients selected from ζ-carotene, neurosporene, spheroidenone, methoxyneurosporene or a combination thereof.

3. The method of claim 1, wherein the Lycogen extract is extracted from a mutant photosynthetic bacterium.

4. The method of claim 3, wherein the mutant photosynthetic bacterium is *Rhodobacter sphaeroides*, which is deposited under deposit number DSM 25056.

5. The method of claim 1, wherein the Lycogen composition has adjunctive effects on cell proliferation, cell migration and/or angiogenesis.

\* \* \* \* \*